United States Patent [19]

Nagahara et al.

[11] Patent Number: 4,734,536
[45] Date of Patent: Mar. 29, 1988

[54] PROCESS FOR PRODUCING CYCLOOLEFINS

[75] Inventors: Hajime Nagahara; Mitsuo Konishi, both of Kurashiki, Japan

[73] Assignee: Asahi Kasei Kogyo Kabushiki Kaisha, Osaka, Japan

[21] Appl. No.: 914,495

[22] Filed: Oct. 2, 1986

[30] Foreign Application Priority Data

Oct. 3, 1985 [JP] Japan .................................. 60-219263
Feb. 28, 1986 [JP] Japan .................................. 60-41981
Jul. 10, 1986 [JP] Japan .................................. 61-160717

[51] Int. Cl.$^4$ ................................................ C07C 5/11
[52] U.S. Cl. ..................... 585/269; 585/266; 585/270; 585/273; 585/274
[58] Field of Search ............... 585/266, 269, 270, 273, 585/274

[56] References Cited

U.S. PATENT DOCUMENTS 3,767,720 10/1973 Drinkard ............................. 585/270
3,912,787 10/1975 Nowalk et al. ...................... 585/270
4,055,512 10/1977 Kageyama et al. .................. 585/270
4,197,415 4/1980 Hideyuki et al. ...................... 585/23
4,392,001 7/1983 Don et al. ............................. 585/269
4,532,351 7/1985 Barneth et al. ...................... 585/270
4,575,572 3/1986 Ichihashi et al. ................... 585/273

FOREIGN PATENT DOCUMENTS 9184138 10/1984 Japan .................................. 585/269
0184031 9/1985 Japan .................................. 585/269
0199637 10/1985 Japan .................................. 585/269

Primary Examiner—Asok Pal
Attorney, Agent, or Firm—Birch, Stewart, Kolasch & Birch

[57] ABSTRACT

A process for producing a cycloolefin in high selectivity and yield by partial hydrogenation of a monocyclic armoatic hydrocarbon with hydrogen is disclosed. In this process, the hydrogenation reaction is carried out under a neutral or acidic condition in the presence of:
(i) a particulate hydrogenating catalyst mainly comprising metallic ruthenium having an average crystallite size of 200 Å or less,
(ii) at least one zinc compound as a promoter,
(iii) at least one additive selected from the group consisting of oxides, hydroxides and hydrates thereof Zr, Hf, Ti, Nb, Ta, Cr, Fe, Co, Al, Ga and Si, and
(iv) water.

37 Claims, No Drawings

PROCESS FOR PRODUCING CYCLOOLEFINS

BACKGROUND OF THE INVENTION

The present invention relates to a process for partially hydrogenating monocyclic aromatic hydrocarbons to produce corresponding cycloolefins, in particular, cyclohexenes in high selectivity and yield.

Cyclohexenes are of high commercial value for use as intermediates for the manufacture of organic chemical engineering products and are particularly important for use as materials for the production of polyamides and lysines. Several methods have been proposed for producing cyclohexenes by reacting aromatic hydrocarbons with hydrogen, and they include: (1) a method using water, an alkali agent, and a catalyst composition containing a reduced cation of group VIII in the periodic table (Japanese Patent Publication No. 22850/1981 and U.S. Pat. No. 3,767,720); (2) a method using a ruthenium catalyst, supported on an oxide of nickel, cobalt, chromium, titanium or zirconium, with an alcohol or an ester being used as an additive (Japanese Patent Publication No. 3933/1977); (3) a method using a Cu, Ag, Co or K-containing ruthenium catalyst, water and a phosphate salt compound, or a method using a catalyst having ruthenium supported on a carrier such as alumina, in combination with water and a phosphate salt compound of cobalt, nickel or copper (Japanese Patent Publication Nos. 4536/1981 and 35646/1981, and U.S. Pat. No. 4,197,415); (4) a method wherein reaction is carried out in the presence of a neutral or acidic aqueous solution containing a ruthenium catalyst and a salt of at least one cation selected from the group consisting of metals of groups IA and IIA in the periodic table and manganese (Japanese Patent Publication No. 7607/1982); (5) a method wherein reaction is carried out in the presence of water using a solid catalyst that is based on at least one of ruthenium and rhodium and which has been preliminarily treated with an aqueous solution containing a salt of at least one cation selected from the group consisting of metals of groups IA and IIA in the periodic table, manganese, iron and zinc (Japanese Laid-open Patent Application No. 98243/1976 and USP 4,055,512); (6) a method wherein reaction is carried out in the presence of a ruthenium catalyst, with at least one of zinc oxide and zinc hydroxide being added to the reaction system as an activator component [Japanese Laid-open Patent Application No. 184138/1984]; and (7) a method using metallic ruthenium crystallites having an average crystallite size of 200 Å or less and/or agglomerated grains thereof in the presence of water and at least one zinc compound [Japanese Laid-open Patent Application No. 50930/1986].

However, in order to enhance the selectivity for the desired cyclohexenes in these prior art methods, the conversion of the monocyclic aromatic hydrocarbons used as starting materials must be considerably reduced and, in addition, the rate of reaction that can be achieved in these methods is very limited. Therefore, the yield and rate of production of cyclohexenes that can be attained in these methods are too low to justify their implementation on a commercial scale.

In order to develop commercial processes for the production of cyclohexenes, it is essential and important that the catalyst used in the reaction should maintain high activity and selectivity in continued operation, but none of the prior art methods have been completely satisfactory in this respect.

According to the studies conducted by the present inventors, if metallic ruthenium crystallites and/or agglomerated grains thereof is used as the sole catalyst as proposed in Japanese Laid-open Patent Application No. 50930/1986, cycloolefins can sometimes be obtained in a comparatively high yield but, on the other hand, difficulty is frequently encountered in maintaining a stable reaction system because of such phenomena as adhesion or deposition of the catalyst on the area of contact between the reactor and the reaction solution and the deterioration of the catalyst per se.

SUMMARY OF THE INVENTION

An object, therefore, of the present invention is to provide a novel process by which a monocyclic aromatic hydrocarbon is partially hydrogenated with hydrogen in the presence of a novel and operationally stable catalyst system composed of a main catalyst and other necessary components, so as to produce a corresponding cycloolefin in high selectivity and yield.

In accordance with the present invention, a monocyclic aromatic hydrocarbon is partially hydrogenated with hydrogen under a neutral or acidic condition in the presence of a particulate hydrogenating catalyst, a promoter and an additive, said particulate hydrogenating catalyst mainly comprising metallic ruthenium having an average crystallite size of 200 Å or less, said promoter being at least one zinc compound, and said additive being at least one member selected from the group consisting of oxides, hydroxides and hydrates thereof of Zr, Hf, Ti, Nb, Ta, Cr, Fe, Co, Al, Ga and Si. This method of the present invention is capable of producing cycloolefins in high yields of 40% or more. In addition, the combination of the particulate hydrogenating catalyst, promoter and additive employed in the present invention is capable of markedly reducing the possibility of retarded reaction due to the deterioration of the hydrogenating catalyst in various ways such as the progress of excess agglomeration of its particles with time and the time-dependent change in their crystallite size. Therefore, the industrial productivity of the process of the present invention for the production of cycloolefins is appreciably higher than that attainable by the prior art methods.

DESCRIPTION OF PREFERRED EMBODIMENTS

Specific embodiments of the present invention are hereunder described in detail. The monocyclic aromatic hydrocarbon used as the starting material in the process of the present invention includes within its category benzene and loweralkylbenzenes, as illustrated by benzene, toluene, xylenes and ethylbenzene.

The process of the present invention also employs a particulate hydrogenating catalyst mainly comprising metallic ruthenium having an average crystallite size of 200 Å or less. The metallic ruthenium that is obtained by reducing a variety of ruthenium compounds or which, during or after its preparation, is applied with other metals such as zinc, chromium, molybdenum, tungsten, manganese, cobalt, nickel, iron or copper. The particulate hydrogenating catalyst contains at least 60 wt. % of metallic ruthenium. Ruthenium compounds which are reduced to obtain metallic ruthenium include ruthenium chlorides, bromides, iodides, nitrates, sulfates, hydroxides, oxides and ruthenium red, as well as various ruthenium-containing complexes. These ruthenium compounds may be reduced either with hydrogen gas or by chemical means, for example, using formalin, sodium borohydride and hydrazine. It is particularly preferable to reduce ruthenium hydroxides that are obtained by hydrolysis of ruthenium salts.

The reduction product of a zinc-containing ruthenium compound may be effectively used as a catalyst in the process of the present invention since it is capable of achieving a further increase in the yield of the product cycloolefin. The catalyst can be obtained by reducing a product prepared by incorporating a zinc compound into a ruthenium compound having cationic ruthenium, and the cationic ruthenium changes to its metallic state by said reduction. Examples of the ruthenium compound having cationic ruthenium include ruthenium salts such as chlorides, nitrates and sulfates, complexes of ruthenium such as ammine complex salts, as well as ruthenium hydroxides and oxides. Tri- or tetra-valent ruthenium compounds are particularly preferable because they are readily available and are easy to handle. A suitable zinc compound may be selected from a broad range of compounds including salts such as chlorides, nitrates and sulfates, complexes such as ammine complex salts, as well as hydroxides and oxides. The zinc content in the catalyst is adjusted to lie within the range of 0.1–50 wt. %, preferably 214 20 wt. %, based on metallic ruthenium. In the present invention, it should be emphasized that the main component of the catalyst is ruthenium and that zinc is not a carrier.

The zinc-containing ruthenium compound may be obtained in a solid form from a mixed solution of a zinc and a ruthenium compound by employing routine procedures of coprecipitation; alternatively, said compound may be obtained in the form of a homogeneous solution.

The zinc-containing ruthenium compound may be reduced by employing customary methods of reduction of ruthenium, such as by reduction with hydrogen in a vapor phase, by reduction with hydrogen or an appropriate chemical reducing agent, such as sodium borohydride and formalin in a liquid phase. Reduction with hydrogen in a vapor or liquid phase is particularly preferable. In performing reduction with hydrogen in a gaseous phase, it is recommended that increases in the crystallite size may be prevented either by avoiding the use of extremely high temperatures or by diluting the hydrogen with an appropriate inert gas. Reduction in a liquid phase may be achieved with a solid zinc-containing ruthenium compound being dispersed in water or an alcohol, or with a homogeneous solution of the zinc-containing ruthenium compound. In the case of liquid-phase reduction, agitation or heating may be applied to a suitable extent in order to achieve through reduction. If desired, water as a liquid medium may be replaced by an aqueous alkaline solution or an aqueous solution of an appropriate metal salt such as an alkali metal salt.

Another effective hydrogenating catalyst is the reduction product of a ruthenium compound containing iron in place of zinc. This type of catalyst can be prepared by techniques similar to those employed in obtaining the reduction product of a zinc-containing ruthenium compound. Usable iron compounds include salts such as iron chlorides, nitrates and sulfates, as well as iron hydroxides and oxides. The iron content of this catalyst is adjusted to lie between 0.01 and 50 wt. %, preferably between 0.1 and 20 wt. %, based on the metallic ruthenium. The main component of this catalyst is also metallic ruthenium.

Details of the partial hydrogenation that is achieved using the iron-containing ruthenium catalyst are found in J. Chem. Tech. Biotechnol., 32, 691–708, 1982. The reaction described in this reference is carried out under alkaline conditions, with cyclohexene being attained in a yield of less than 20% at maximum. Therefore, this method of prior art differs entirely from the present invention not only with respect to the conditions employed but also in terms of the results attained.

The particulate hydrogenating catalyst described above is present in the reaction system in the form of ruthenium-based crystallites and/or agglomerated particles thereof. In order to increase the selectivity and yield of cycloolefins and to provide an enhanced rate of reaction, the average size of said crystallites must not be greater than 200 Å, with sizes of 150 Å or less being preferable. More preferably, the average size of crystallites is 100 Å or below. It will be more preferable if the average size of the crystallite is as small as possible, and the lower limit of the size is the theoretical one of the crystallite unit of the metallic ruthenium. The average crystallite size may be determined by common procedures, namely by applying Scherrer's equation to the X-ray diffraction line broadening. Stated more specifically, the average crystallite size may be calculated from the X-ray diffraction line broadening of a peak at $2\theta$ of about 44° ($2\theta$=angle of diffraction), with CuK$\alpha$ radiation being used as a source of X-rays. While the average size of crystallites in metallic ruthenium can be verified by the method of X-ray diffraction described above, the practical lower limit for the calculation of the average crystallite size is about 20 Å.

In the process of the present invention, hydrogenation is carried out with the particulate hydrogenating catalyst being used in an amount of 0.001–50 wt. %, preferably 0.01–20 wt. %, based on the monocyclic aromatic hydrocarbon fed.

It is essential for attaining the purpose of the present invention that at least one zinc compound be present as a promoter in the reaction system. The zinc compound may be water-soluble or sparingly water-soluble and many candidates exist as usable zinc compounds. Illustrative water-soluble zinc compounds include salt of strong acids such as zinc sulfate, zinc chloride and zinc nitrate, salts with weak acids such as zinc acetate, and various ammonium complexes, with aqueous solutions of zinc salts of strong acids being preferably used. The use of water-soluble zinc compounds in combination with the particulate hydrogenating catalyst is effective in improving the selectivity for cycloolefins and this effect is pronounced if zinc salts of strong acids are used. The use of zinc sulfate is most preferable for this purpose. Zinc salts of strong acids need not be completely dissolved in the reaction system but their concentration in an aqueous solution generally ranges from $1 \times 10^{-3}$ wt. % to the saturated concentration thereof. It is more preferable to use an aqueous solution of zinc sulfate in the concentration range of 0.1–30 wt. %.

Several pronounced effects can be attained by using a basic zinc salt, which is a sparingly watersoluble zinc compound, in a solid form as the promoter. The term "basic zinc salt" covers zinc salts that contain both conjugated base residues of various acids and a hydroxyl group or an oxygen atom each of which can be regarded as another negative component; basic zinc salts included within this category are basic zinc sulfate derivatives such as $ZnSO_4 \cdot \frac{1}{2}ZnO$, $ZnSO_4 \cdot ZnO \cdot H_2O$, $ZnSO_4 \cdot Zn(OH)_2$, $Zn_2(OH)_2SO_4$, $ZnSO_4 \cdot 3ZnO$, $ZnSO_4 \cdot 3ZnO \cdot 3H_2O$, $ZnSO_4 3Zn(OH)_2$, $ZnSO_4 \cdot 3ZnO \cdot 6H_2O$, $ZnSO_4 \cdot 3ZnO \cdot 7H_2O$, $ZnSO_4 \cdot 3ZnO \cdot 8H_2O$, $ZnSO_4 \cdot 4ZnO \cdot 4H_2O$, $ZnSO_4 \cdot 4Zn(OH)_2$; basic zinc halide derivatives such as $ZnO \cdot ZnCl_2 \cdot nH_2O$ (n=1 or 1.5), $ZnO \cdot 3ZnCl_2 \cdot H_2O$, $3ZnO \cdot 2ZnCl_2 \cdot 11H_2O$, $2ZnO \cdot ZnCl_2 \cdot 4H_2O$, $5ZnO \cdot 2ZnCl_2 \cdot 26H_2O$, $5ZnO \cdot 5ZnCl_2 \cdot 8H_2O$, $3ZnO \cdot ZnCl_2 \cdot nH_2O$ (n=2, 3, 4, 5 or 8), $4ZnO \cdot ZnCl_2 \cdot nH_2O$ (n=4, 6 or 11), $9ZnO \cdot 2ZnCl_2 \cdot 12H_2O$, $5ZnO \cdot ZnCl_2 \cdot nH_2O$ (n=6, 8 or 29), $11ZnO \cdot 2ZnCl_2$, $6ZnO \cdot ZnCl_2 \cdot nH_2O$ (n=6 or 10), $8ZnO \cdot ZnCl_2 \cdot 10H_2O$, $9ZnO \cdot ZnCl_2 \cdot nH_2O$ (n=3 or 14), $ZnBr_2 \cdot 4ZnO \cdot nH_2O$ (n=10, 13, or 29), $ZnBr_2 \cdot 5ZnO \cdot 6H_2O$, $ZnBr_2 \cdot 6ZnO \cdot 35H_2O$, $ZnI_2 \cdot 4Zn(OH)_2$, $ZnI_2 \cdot 5ZnO \cdot 11H_2O$, and $ZnI_2 \cdot 9ZnO \cdot 24H_2O$; basic zinc nitrate derivatives such as $8ZnO \cdot N_2O_5 \cdot 4H_2O$, $4ZnO \cdot N_2O_5 \cdot 4H_2O$, $5ZnO \cdot N_2O_5 \cdot nH_2O$ (n=5 or 6), and $5ZnO \cdot N_2O_5 \cdot H_2O$, and basic zinc acetate derivatives. Among these derivatives, basic zinc sulfate and basic zinc chloride derivatives are preferably used, with basic zinc sulfate derivatives, being particularly preferable.

The basic zinc salts given above may be generally prepared by appropriately treating aqueous solutions of zinc salts. In one method, a solid form of a basic zinc salt is obtained from an aqueous solution of a zinc salt by causing an appropriate alkali agent to act on the latter, which may be subsequently heated as required. In an alternative method, a mixture of two or more basic zinc salts may be obtained by boiling an aqueous solution of a zinc salt of a strong acid after zinc hydroxide or oxide has been added thereto. Metallic zinc may be appropriately treated to attain a desired basic zinc salt.

In order to have the aforementioned basic zinc salts present in a solid form in the reaction system, it is preferable that one or more of these salts in a powder form are mixed with the particulate hydrogenating catalyst and the additive (to be described later in this specification) before they are charged into a reactor, alternatively, such salts may be added to the reaction system separately from the particulate hydrogenating catalyst and the additive.

In performing the method of the present invention, it is preferable that the aforementioned basic zinc salts are present in an undissolved state. The solubility of the basic zinc salts in water is practically negligible if the latter is neutral in nature but increases with decreasing pH. For this reason, the amounts of these basic zinc salts to be added to the reaction system are preferably determined in consideration of the pH condition. It should however be noted that because of the adsorptive power of the hydrogenating catalyst mainly comprising metallic ruthenium used in the present invention, the basic zinc salts will often remain solid on that catalyst even if they are present in the reaction system in amounts less than the saturated concentration thereof.

In accordance with the present invention, hydrogenation is carried out with the solid basic zinc salts being present in amounts as zinc element ranging from $1 \times 10^{-4}$ to 1, preferably from $1 \times 10^{-3}$ to 0.5 times by weight based on the total weight of the particulate hydrogenating catalyst and the additive. If the amount of the solid basic zinc salt added is smaller than the lower limit, the desired effects of the salt to be described later in this specification will not be attained. If, on the other hand, the amount of the solid basic zinc salt added is greater than the upper limit, the rate of reaction is reduced to such a level that an excessive amount of the particulate hydrogenating catalyst must eventually be used, which is by no means desirable for practical purposes.

The existence of the aforementioned solid basic zinc salt can be directly verified by an appropriate method such as X-ray diffraction, X-ray fluorescence or X-ray photoelectron spectroscopy, which are applied to a mixture of said basic zinc salt in a solid form with the ruthenium catalyst and the additive after being separated from the reaction system. Quantitative analysis of said basic zinc salt is preferably performed by measuring its amount in a solution of the solid mass that has been separated from the reaction system together with the ruthenium catalyst and the additive. Stated more specifically, quantitative determination of the solid basic zinc salt may be achieved by the following procedures; the solid component is sedimentated from the liquid reaction mixture and the supernatant is removed to obtain the residual slurry; or alternatively, the slurry in the reaction mixture is filtered to recover a solid mass; to either the residual slurry or solid mass, a liquid such as concentrated hydrochloric acid that is capable of dissolving the basic zinc salts which are not dissolved in the reaction system is added, and the mixture is subjected to routine procedures for assaying and determining zinc ions. For attaining various purposes such as eliminating any adverse effects that may be exerted upon the accuracy of analysis by concomitant ions in the reaction system, the slurry or the filter cake may be washed with a very small amount of water which will dissolve only a negligible amount of the basic zinc salt before concentrated hydrochloric acid or any other appropriate reagent is added to initiate quantitative determination of zinc ions.

If the solid basic zinc salt is incorporated in the reaction system together with the hydrogenating catalyst in the manner described above, significant advantages will result as set forth below, with maximum effect being attainable by using a basic zinc sulfate derivative.

First of all, the selectivity and yield of the product cycloolefins can be increased by using the solid basic zinc salt, in particular, the solid basic zinc sulfate. This effect is similar to that attained by the already-mentioned water-soluble zinc compound. Another advantage that results from using the solid basic zinc salt, in particular, the solid basic zinc sulfate, is that the range of reaction temperature that provide comparably high levels of selectivity and yield is extended such that cycloolefins can be attained in good yield even at relatively low temperatures. This leads to a greater latitude in selecting optimal reaction conditions and helps to provide a process of industrially high value that is capable of efficient production of cycloolefins.

A further increase in the selectivity and yield of cycloolefins can be realized by using an aqueous solution of a zinc salt of a strong acid in combination with one or more of the solid basic zinc salts described above. A particularly great effect is attained by combining an aqueous solution of zinc sulfate with the solid basic zinc sulfate.

If the basic zinc sulfate is present in the aqueous solution of zinc sulfate, equilibrium is established between the solubilities of the ions and compounds present and, although the aqueous solution of zinc sulfate is acidic, only a trace amount of the basic zinc sulfate will dissolve in that solution, thereby allowing the basic zinc sulfate to remain undissolved throughout the reaction. To take an example, if $ZnSO_4 \cdot 3Zn(OH)_2$ is added to a 10% aqueous solution of zinc sulfate (a pH value of about 5) in an amount of several tens of ppm with respect to water, the pH of the solution is stabilized in the neighborhood of 5.7-5.8, thereby allowing $ZnSO_4.3Zn(OH)_2$ to remain undissolved in water. As will be apparent from this example, the presence of the basic zinc sulfate in an aqueous solution of zinc sulfate also serves to shift the pH of the aqueous solution toward neutrality and this is expected to offer favorable conditions for the metallic part of the reactor and associated equipment which would otherwise be attacked by corrosion if the aqueous solution of zinc sulfate is acidic in nature.

The presence of the solid basic zinc salt has the additional advantage of enhancing the meritorious effect of the additive which, as will be described immediately below, constitute another essential element of the present invention. This additional advantage of the solid basic zinc salt present in the reaction system will be described later in this specification.

In the process of the present invention, hydrogenation reaction is carried out with at least one of oxides, hydroxides and hydrates thereof of Zr, Hf, Ti, Nb, Ta, Cr, Fe, Co, Al, Ga and Si being present in addition to the particulate hydrogenating catalyst and the promoter of at least one zinc compound. A part or all of such oxide may be in a state of a hydroxide and/or a hydrate thereof, and this case is also included within the scope of the present invention.

The additive described above is added in amounts ranging from $1 \times 10^{-3}$ to 0.3 times by weight, preferably from $1 \times 10^{-2}$ to 0.1 times by weight, based on the weight of the water present in the reaction system.

The additives is preferably in a fine powder form, with the average particle size ranging from 0.005 to 100 $\mu$m, more preferably from 0.005 to 10 $\mu$m. The average particle size of the additive is determined by the following procedures; the additive is dispersed in ethanol in an amount of no more than 1 wt. % of the dispersion medium; a dispersion is formed by treatment in an ultrasonic generator (<1,000 W) for a period of 30-60 minutes; then the change in the light absorbance of the dispersion that occurs as a result of sedimentation achieved by routine methods (i.e., gravitational sedimentation and centrifugal sedimentation) is checked to calculate the average particle size of the additive.

The addition of the additive described above in the reaction system has the advantage of facilitating the general procedures of handling the catalyst-containing slurry by, first of all, markedly suppressing the change of the reaction system owing to the agglomeration of the hydrogenating catalyst and to its adhesion to the metallic surface of the inner-wall of the reactor and, secondly, by diluting the hydrogenating catalyst to achieve an apparent increase in its volume so as to provide greater ease in effecting the operations of charging and recovering the catalyst. A particularly great effect is attained with respect to the reaction system which can be stabilized by using the metal oxide, the metal hydroxide or the hydrate thereof, as specifically described below.

The particulate hydrogenating catalyst mainly comprising metallic ruthenium is used in the present invention while it is finely dispersed in the reaction system, particularly in its aqueous phase. Unlike a metallic catalyst supported on a carrier, a fine particulate metallic catalyst will often experience agglomeration of the individual particles to form secondary particles or even sintering of the primary particles during the reaction and, hence, cannot be consistently used as an active catalyst system for an extended period. Actually, when the process of the present invention is conducted without adding either a metal oxide, a metal hydroxide or a hydrate thereof, the particulate hydrogenating catalyst will often agglomerate and adhere to the metallic inner-wall of the reactor, as a result, not only the rate and selectivity of the hydrogenation decrease but the stabilized reaction system can not be maintained. Furthermore, the average crystallite size of the metallic ruthenium within the particulate hydrogenating catalyst increases to cause a reduced surface area of the catalyst and a slowing down of the rate of the hydrogenation. The phenomena mentioned above become more remarkable according to the raise of the concentration of the catalyst or of the reaction temperature. The tendency described above obstructs the improvement of the productivity of cycloolefin per volume of a reactor. On the contrary, in the reaction system employed in the process of the present invention which incorporates the metal oxide, the metal hydroxide and/or the hydrate thereof, agglomeration of the particles of the hydrogenating catalyst and their adhesion to the metallic surface of the reactor are effectively inhibited to ensure consistent performance in reaction and the concentration of the hydrogenating catalyst and the reaction temperature can be increased without causing any considerable time-dependent increase in the average crystallite size of metallic ruthenium. This stabilizing effect of the additive can be enhanced by using it in combination with the aforementioned solid basic zinc salt, in particular, the basic zinc sulfate and, as a result, the increase in the average crystallite size of metallic ruthenium can be reduced to a virtually negligible level. In all likelihood, the additive will greatly inhibit the particles of the hydrogenating catalyst from colliding with one another and will sometimes collide against the particles of hydrogenating catalyst to enhance the state of their dispersion, thereby serving to greatly reduce the chance of the catalyst particles agglomerating together to form secondary particles, which phenomenon can be an indirect cause of the catalyst having a reduced surface area or the metallic ruthenium in the catalyst assuming an increased crystallite size. In addition, any solid basic zinc salt present would be deposited on the surfaces of the hydrogenating catalyst and the additive to cause a change in their surface properties.

Preferable examples of the additive are $ZrO_2$ and $HfO_2$, both of which serve to achieve a further improvement in the selectivity and yield of the product cycloolefins.

It should be stated here that if a catalyst prepared by reducing a ruthenium compound that is supported on the aforementioned metal oxide by a conventional method such as dipping, evaporation to dryness or precipitation is used as a hydrogenating catalyst, the selectivity for the product cycloolefins is extremely small compared with that attained by the process of the present invention. Therefore, the addition of the metal oxide as achieved in the present invention differs in essence from the use of a ruthenium-carrying catalyst.

Water is another essential component for the practice of the present invention. The amount of water to be added varies with the type of reaction to be carried out and, generally, water may be present in an amount of 0.01-100 times by weight based on the weight of the monocyclic aromatic hydrocarbon fed. Preferably, two separate phases, one being the organic liquid phase mainly composed of the starting materials and the product and the other being the water-containing liquid phase, are formed under the reaction conditions employed. The purposes of the present invention will not be effectively attained if the amount of water present is either very small or extremely large such as to provide a homogeneous phase under the reaction conditions employed. In addition, the presence of an excessive amount of water necessitates the use of a large reactor. Therefore, in practical applications, water is desirably present in an amount of 0.5–2.0 times by weight based on the weight of the monocyclic aromatic hydrocarbon fed. Water may be used in the form of an aqueous solution of a suitable metal salt as effected in prior art methods, and illustrative metal salts are strong acid salts of metals of groups IA and IIA in the periodic table.

In the process of the present invention, hydrogenating reaction must be carried out with the aqueous phase present being held under either a neutral or acidic condition. If the aqueous phase becomes alkaline, the rate of reaction will be decreased to an undesirably low level. The pH of the aqueous phase should generally be within the range of 0.5–7, preferably 0.5 to less than 7, and more preferably 2–6.5.

In the process of the present invention, partial hydrogenation is typically carried out either continuously or batch-wise by the liquid-phase suspension method but it may be performed in a fixed-phase mode. The reaction conditions should be properly determined in accordance with the types and amounts of the catalyst and additives used; usually, the hydrogen pressure is within the range of 1–200 Kg/cm$^2$G, preferably between 10 and 100 Kg/cm$^2$G, and the reaction temperature is within the range of 20° C. to 250° C., preferably between 100° and 200° C. The duration of the reaction time is not limited to any particular value and may be properly determined on the basis of the practical targets of the selectivity and yield of the desired cyclohexenes; in the usual case, the reaction time ranges from several seconds to several hours.

The present invention is hereunder described in greater detail with reference to working examples but it should be noted that the scope of the present invention is by no means limited to these particular examples.

In Examples, the conversion of a monocyclic aromatic hydrocarbon, selectivity for a cycloolefin and yield of a cycloolefin are those obtained by the following formula:

$$\text{Conversion of a monocyclic aromatic hydrocarbon (\%)} = \frac{\text{(mole number of consumed monocyclic aromatic hydrocarbon)}}{\text{(mole number of fed monocyclic aromatic hydrocarbon)}} \times 100 \quad (1)$$

$$\text{Selectivity for a cycloolefin (\%)} = \frac{\text{(mole number of produced cycloolefin)}}{\text{(mole number of consumed monocyclic aromatic hydrocarbon)}} \quad (2)$$

$$\text{Yield of a cycloolefin (\%)} = \frac{\text{(mole number of produced cycloolefin)}}{\text{(mole number of fed monocyclic aromatic hydrocarbon)}} \quad (3)$$

EXAMPLE 1

To a 1 l of a 1% aqueous solution of ruthenium chloride (RuCl$_3$.3H$_2$O) vigorously stirred with a stirrer equipped with Teflon-coated turbine blades, 150 ml of a 30% aqueous sodium hydroxide solution was added instantaneously and the resulting mixture was agitated at 80° C. for an additional 3 hours. After the mixture had been cooled to about 25° C., it was left to stand and the supernatant was removed. The remaining black precipitate was diluted with water to 500 ml and the resulting aqueous solution was charged into an autoclave (capacity, 1,000 ml) the inner surface of which had been coated with Teflon. The autoclave was filled with hydrogen to raise the total internal pressure to 50 Kg/cm$^2$G and reduction was conducted at 150° C. for 5 hours. The reaction mixture was filtered in an argon atmosphere, washed several times with water and dried at 80° C. in an argon atmosphere to obtain 3.7 g of a hydrogenating catalyst composed of metallic ruthenium. The average crystallite size of this catalyst was calculated as 50 Å by an X-ray diffraction spectrum.

A portion (0.4 g) of this catalyst, 320 ml of water, 14.4 g of ZnSO$_4$.7H$_2$O, 2.0 g of a ZrO$_2$ powder (UEP of Daiichi Kigenso Kagaku Kogyo K.K.; average particle size, 0.35 μm) and 80 ml of benzene were charged into an autoclave (inner capacity, 1,000 ml) the inner surface of which had been coated with Teflon. After the temperature in the autoclave was elevated to 150° C., a hydrogen gas was introduced into the autoclave to attain a total internal pressure of 50 Kg/cm$^2$G and reaction was carried out with high-speed agitation. The reaction mixture was withdrawn from the autoclave at predetermined times and subjected to gas chromatography for analysis of the composition of the oil phase. The results are shown below.

| Time of reaction (min.) | Conversion of benzene (%) | Selectivity for cyclohexene (%) | Yield of cyclohexene (%) |
|---|---|---|---|
| 21 | 30 | 86.2 | 25.9 |
| 62 | 60 | 79.6 | 47.8 |

Cyclohexane was formed as a by-product.

COMPARATIVE EXAMPLE 1

The procedures of example 1 were repeated except that the ZrO$_2$ powder was not used. The results are shown below.

| Time of reaction (min.) | Conversion of benzene (%) | Selectivity for cyclohexene (%) | Yield of cyclohexene (%) |
|---|---|---|---|
| 19 | 30 | 71.0 | 21.3 |
| 54 | 60 | 54.0 | 32.4 |

COMPARATIVE EXAMPLE 2

The procedures of Example 1 were repeated except that the amount of the hydrogenating catalyst used was decreased to 0.04 g and that neither a ZrO$_2$ powder nor ZnSO$_4$.7H$_2$O was used. The results are shown below.

| Time of reaction (min.) | Conversion of benzene (%) | Selectivity for cyclohexene (%) | Yield of cyclohexene (%) |
|---|---|---|---|
| 8 | 30 | 5.8 | 1.7 |
| 21 | 60 | 2.6 | 1.6 |

EXAMPLE 2

A hydrogenating catalyst with an average crystallite size of 43 Å was prepared as in Example 1 except that the time of reduction reaction was shortened to 2 hours. Hydrogenation was conducted as in Example 1 except that 0.4 g of this catalyst was employed. The results are shown in Table 1.

EXAMPLE 3

A hydrogenating catalyst with an average crystallite size of 135 Å was prepared as in Example 1 except that the black precipitate was dried and reduced in a hydrogen stream after filtration. Hydrogenation was conducted as in Example 1 except that 0.4 g of this catalyst was employed. The results are shown in Table 1.

EXAMPLE 4

Five grams of ruthenium chloride ($RuCl_3.3H_2O$) and 13.0 g of zinc chloride were dissolved in 500 ml of water with agitation. To the stirred solution, 70 ml of a 30% aqueous sodium hydroxide solution was added instantaneously and the resulting mixture was agitated for an additional 2 hours at 80° C. After being cooled, the mixture was left to stand and the black precipitate was washed three times with an aqueous solution of 1N NaOH after the supernatant had been removed by decantation. The greater part of the washed black precipitate was $Zn(OH)_2$-containing $Ru(OH)_3$, with part of it being present in the form of a chloride. This black precipitate was dispersed in 500 ml of a 5% aqueous sodium hydroxide solution and charged into an autoclave (inner capacity, 1,000 ml) the inner surface of which had been coated with Teflon. Hydrogen was introduced into the autoclave to raise the total internal pressure to 50 Kg/cm²G and reduction was conducted at 150° C. for 12 hours. The reaction mixture was cooled and the obtained black powder was washed in an argon atmosphere first with 30% aqueous NaOH, then with water, and subsequently vacuum-dried to obtain 2.3 g of a hydrogenating catalyst. Analysis by X-ray diffraction showed that the crystallites in the catalyst had grown to an average size of 55 Å. The zinc content of this catalyst as determined by X-ray fluorescence was 7.4 wt. %. Hydrogenation was conducted as in Example 1 except that 0.4 g of the catalyst was employed. The results are shown in Table 1.

EXAMPLE 5

Ruthenium chloride ($RuCl_3.3H_2O$, 1.56 g) and zinc sulfate ($ZnSO_4.7H_2O$, 0.26 g) were dissolved in 500 ml of water with agitation. To the stirred solution, 0.9 g of sodium borohydride in 100 ml of water was added and reduction reaction was carried out. The reaction mixture was washed and dried to obtain 0.6 g of a hydrogenating catalyst. This catalyst had a zinc content of 2.6 wt. % and an average crystallite size of 40 Å.

Hydrogenation of benzene was conducted at in Example 1 using the above-prepared hydrogenation catalyst. The results are shown in Table 1.

EXAMPLE 6

A hydrogenation catalyst having an average crystallite size of 46 Å and a zinc content of 15.0 wt. % was prepared by appropriately modifying the preparation conditions employed in Example 4.

Hydrogenation of benzene was conducted as in Example 1 except that 0.4 g of said catalyst was used. The results are shown in Table 1.

EXAMPLE 7

The procedures of Example 4 were repeated except that the $ZrO_2$ powder was replaced by 2.0 g of a $HfO_2$ powder (product of Wako Pure Chemical Industries, Ltd.; average particle size, 1.05 μm). The results are shown in Table 1.

EXAMPLE 8

The procedures of Example 4 were repeated except that the $ZnSO_4.7H_2O$ was replaced by 6.7 g of $ZnCl_2$. The results are shown in Table 1.

EXAMPLE 9

The procedures of Example 4 were repeated except that the $ZnSO_4.7H_2O$ was replaced by 2.0 g of $Zn(CH_3CO_2)_2$. The results are shown in Table 1.

TABLE 1

| Run No. | Hydrogenating catalyst Average crystallite size (Å) | Zn content (wt. %) | Metal oxide | Water-soluble zinc compound | Reaction time (min.) | Conversion of benzene (%) | Selectivity for cyclohexene (%) | Yield of cyclohexene (%) |
| --- | --- | --- | --- | --- | --- | --- | --- | --- |
| 2 | 43 | — | $ZrO_2$ | $ZnSO_4.7H_2O$ 14.4 g | 21 57 | 30 60 | 86.8 80.0 | 26.0 48.0 |
| 3 | 135 | — | $ZrO_2$ | $ZnSO_4.7H_2O$ 14.4 g | 49 135 | 30 60 | 86.7 79.1 | 26.0 47.5 |
| 4 | 55 | 7.4 | $ZrO_2$ | $ZnSO_4.7H_2O$ 14.4 g | 23 64 | 30 60 | 88.8 83.0 | 26.6 49.8 |
| 5 | 40 | 2.6 | $ZrO_2$ | $ZnSO_4.7H_2O$ 14.4 g | 28 70 | 30 60 | 86.3 80.7 | 25.9 48.4 |
| 6 | 46 | 15.0 | $ZrO_2$ | $ZnSO_4.7H_2O$ 14.4 g | 35 95 | 30 60 | 87.1 81.1 | 26.1 48.7 |
| 7 | 55 | 7.4 | $HfO_2$ | $ZnSO_4.7H_2O$ 14.4 g | 24 66 | 30 60 | 88.4 82.9 | 26.5 49.7 |
| 8 | 55 | 7.4 | $ZrO_2$ | $ZnCl_2$ 6.7 g | 27.5 69 | 30 60 | 87.8 82.8 | 26.3 49.7 |
| 9 | 55 | 7.4 | $ZrO_2$ | $Zn(CH_3CO_2)_2$ 2.0 g | 43 122 | 30 60 | 77.5 68.6 | 23.3 41.2 |

COMPARATIVE EXAMPLES 3-4

Ruthenium was adsorbed on a $ZrO_2$ powder (Comparative Example 3) and a $HfO_2$ powder (Comparative Example 4) by routine procedures, and each of the samples was reduced with hydrogen to prepare 4.0 g of a hydrogenating catalyst carrying 1 wt. % of metallic ruthenium. Using this catalyst, hydrogenation of benzene was conducted as in Example 1 except that no $ZrO_2$ was added. The results are shown in Table 2.

TABLE 2

| Run No. | Hydrogenating catalyst | Reaction time (min.) | Conversion of benzene (%) | Selectivity for cyclohexene (%) | Yield of cyclohexene (%) |
|---|---|---|---|---|---|
| 3 | Ru/ZrO$_2$ | 26.5 | 30 | 32.4 | 9.7 |
|   |   | 60.5 | 60 | 18.6 | 11.2 |
| 4 | Ru/HfO$_2$ | 21.5 | 30 | 28.8 | 8.6 |
|   |   | 56.0 | 60 | 15.3 | 9.2 |

The above data shows that the catalyst system used in the process of the present invention differs entirely from the conventional ruthenium-carrying catalyst systems.

EXAMPLES 10–21

The stability of present catalyst systems was examined by the following procedures. One half gram of a hydrogenating catalyst (average crystallite size, 51 Å; zinc content, 4.8 wt. %), 280 ml of water, 28.8 g of ZnSO$_4$.7H$_2$O, 140 ml of benzene and 3.5 g of a metal oxide powder or hydrated product thereof (for their types and average particle sizes, see Table 3) were charged into an autoclave (inner capacity, 1,000 ml), which was made of titanium at the inner surface of the wall and any other portions such as agitating blades that would be contacted with the reaction solution. Hydrogenation of benzene was conducted for 120 minutes with high-speed agitation at 150° C. and at a hydrogen pressure of 50 Kg/cm$^2$G. Thereafter, only the oil phase was extracted from the autoclave and hydrogenation was performed for an additional 120 minutes, with 140 ml of fresh benzene supplied. This operation was performed repeatedly and at the 5th and 10th cycles, the reaction mixture was withdrawn from the autoclave and subjected to gas chromatography for analyzing the composition of the oil phase. The results observed after 60 minutes of reaction for each run are summarized in Table 3.

EXAMPLES 22–26

A hydrogenating catalyst having an average crystallite size of 51 Å and an iron content of 2.4 wt. % was prepared as in Example 4 except that the zinc chloride was replaced by 1.1 g of ferric chloride. Hydrogenation of benzene was conducted as in Examples 10 to 21 except that 0.7 g of this catalyst was used. The results observed after 60 minutes of reaction for each run are summarized in Table 4.

TABLE 4

| Run No. | Additive | Cycle times | Conversion of benzene (%) | Selectivity for cyclohexene (%) | Yield of cyclohexene (%) |
|---|---|---|---|---|---|
| 22 | ZrO$_2$ | 5 | 59.5 | 77.3 | 46.0 |
|    |    | 10 | 59.0 | 77.5 | 45.7 |
| 23 | Nb$_2$O$_5$ | 5 | 60.2 | 69.0 | 41.5 |
|    |    | 10 | 58.8 | 69.8 | 41.0 |
| 24 | Cr$_2$O$_3$ | 5 | 54.6 | 76.9 | 42.0 |
|    |    | 10 | 54.2 | 77.0 | 41.7 |
| 25 | γ-Al$_2$O$_3$ | 5 | 66.1 | 63.4 | 41.9 |
|    |    | 10 | 64.2 | 65.8 | 42.2 |
| 26 | SiO$_2$ | 5 | 57.1 | 72.1 | 41.2 |
|    |    | 10 | 55.2 | 72.8 | 40.2 |

EXAMPLES 27–31

Hydrogenation of benzene was conducted by repeating the procedures of Examples 10 to 21 except that the hydrogenating catalyst used was 0.7 g of a fine particu-

| Run No. | Additive | Average particle size (μm) | Cycle times | Conversion of benzene (%) | Selectivity for cyclohexene (%) | Yield of cyclohexene (%) |
|---|---|---|---|---|---|---|
| 10 | ZrO$_2$[a] | 0.35 | 5 | 64.4 | 77.7 | 50.0 |
|    |    |    | 10 | 64.0 | 78.0 | 49.9 |
| 11 | HfO$_2$[b] | 1.05 | 5 | 63.5 | 76.9 | 48.8 |
|    |    |    | 10 | 62.6 | 77.1 | 48.3 |
| 12 | TiO$_2$[b] | 1.0 | 5 | 66.3 | 70.7 | 46.9 |
|    |    |    | 10 | 65.8 | 71.2 | 46.8 |
| 13 | Nb$_2$O$_5$[b] | 15 | 5 | 65.2 | 72.1 | 47.0 |
|    |    |    | 10 | 64.3 | 72.8 | 46.8 |
| 14 | Ta$_2$O$_5$[b] | 13 | 5 | 58.0 | 78.0 | 45.2 |
|    |    |    | 10 | 57.2 | 78.4 | 44.8 |
| 15 | Cr$_2$O$_3$[b] | 2.1 | 5 | 53.1 | 81.6 | 43.3 |
|    |    |    | 10 | 52.5 | 81.9 | 43.0 |
| 16 | Fe$_2$O$_3$[b] | 1.5 | 5 | 60.5 | 76.5 | 46.3 |
|    |    |    | 10 | 59.4 | 77.0 | 45.7 |
| 17 | Co$_3$O$_4$[b] | 2.0 | 5 | 49.7 | 81.8 | 40.7 |
|    |    |    | 10 | 48.3 | 82.1 | 39.7 |
| 18 | γ-Al$_2$O$_3$[b] | 1.3 | 5 | 67.8 | 69.2 | 46.9 |
|    |    |    | 10 | 65.4 | 70.8 | 46.3 |
| 19 | Ga$_2$O$_3$[b] | 12 | 5 | 64.2 | 74.2 | 47.6 |
|    |    |    | 10 | 63.8 | 74.5 | 47.5 |
| 20 | SiO$_2$[b] | 3.5 | 5 | 65.2 | 73.0 | 47.6 |
|    |    |    | 10 | 64.5 | 73.2 | 47.2 |
| 21 | ZrO$_2$.XH$_2$O[c] | 0.08 | 5 | 52.1 | 81.3 | 42.4 |
|    |    |    | 10 | 50.0 | 82.6 | 41.3 |

[a] Product of Daiichi Kigenso Kagaku Kogyo K.K.
[b] Product of Wako Pure Chemical Industries, Ltd.
[c] Hydrolyzed product of ZrOCl$_2$; added in an amount of 3.5 g in term of ZrO$_2$.

late metallic ruthenium having an average crystallite size of 55 Å. The results observed after 60 minutes of reaction for each run are summarized in Table 5.

TABLE 5

| Run No. | Additive | Cycle times | Conversion of benzene (%) | Selectivity for cyclohexene (%) | Yield of cyclohexene (%) |
| --- | --- | --- | --- | --- | --- |
| 27 | $ZrO_2$ | 5 | 64.8 | 72.0 | 46.7 |
|  |  | 10 | 63.6 | 72.1 | 45.9 |
| 28 | $Nb_2O_6$ | 5 | 71.6 | 55.6 | 39.8 |
|  |  | 10 | 69.3 | 56.8 | 39.4 |
| 29 | $Cr_2O_3$ | 5 | 63.1 | 70.6 | 44.5 |
|  |  | 10 | 60.5 | 71.8 | 43.4 |
| 30 | $\gamma$-$Al_2O_3$ | 5 | 80.8 | 42.7 | 34.5 |
|  |  | 10 | 78.0 | 45.0 | 35.1 |
| 31 | $SiO_2$ | 5 | 64.6 | 61.9 | 40.0 |
|  |  | 10 | 62.1 | 63.0 | 39.1 |

COMPARATIVE EXAMPLE 5

The procedures of Examples 27 to 31 were repeated except that no metal oxide was added during the hydrogenation of benzene. The results are shown below.

| Cycle times | Reaction time (min.) | Conversion of benzene (%) | Selectivity for cyclohexene (%) | Yield of cyclohexene (%) |
| --- | --- | --- | --- | --- |
| 5 | 80 | 57.3 | 58.1 | 33.5 |
| 10 | 90 | 35.2 | 67.7 | 23.8 |

COMPARATIVE EXAMPLES 6-17

Samples of hydrogenating catalyst (5.0 g) which carried 1 wt. % of ruthenium were prepared by reducing with hydrogen the ruthenium chloride adsorbed on the metal oxides or hydrated product thereof that were the same as those employed in Examples 10 to 21 (see Table 3). Hydrogenation of benzene was conducted as in Examples 10 to 21 except that no metal oxide was added. The results of reaction at cycle time 5 are summarized in Table 6.

The data in Table 6 shows that the selectivity and yield of cyclohexene attained by each of the ruthenium-carrying catalysts were much lower than those achieved by the catalyst system used in the process of the present

TABLE 6

| Run No. | Hydrogenating catalyst | Reaction time (min.) | Conversion of benzene (%) | Selectivity for cyclohexene (%) | Yield of cyclohexene (%) |
| --- | --- | --- | --- | --- | --- |
| 6 | $Ru/ZrO_2$ | 80 | 61.8 | 20.3 | 12.5 |
| 7 | $Ru/HfO_2$ | 80 | 62.9 | 17.0 | 10.7 |
| 8 | $Ru/TiO_2$ | 50 | 73.9 | 1.1 | 0.8 |
| 9 | $Ru/Nb_2O_5$ | 60 | 64.1 | 2.1 | 1.3 |
| 10 | $Ru/Ta_2O_5$ | 60 | 54.5 | 2.0 | 1.1 |
| 11 | $Ru/Cr_2O_3$ | 100 | 26.8 | 4.8 | 1.3 |
| 12 | $Ru/Fe_2O_3$ | 60 | 29.0 | 18.8 | 5.5 |
| 13 | $Ru/Co_3O_4$ | 60 | 20.3 | 25.8 | 5.2 |
| 14 | $Ru/\gamma$-$Al_2O_3$ | 30 | 71.4 | 13.2 | 9.4 |
| 15 | $Ru/Ga_2O_3$ | 30 | 56.4 | 20.4 | 11.5 |
| 16 | $Ru/SiO_2$ | 30 | 63.0 | 12.9 | 8.1 |
| 17 | $Ru/ZrO_2.XH_2O$ | 110 | 50.5 | 30.7 | 15.5 |

EXAMPLES 32-37

One half gram of the same hydrogenating catalyst as prepared in Example 1, 2.5 g of a $ZrO_2$ powder, 100 mg (as Zn) of one of the basic zinc salts listed in Table 7, and 280 ml of water were charged into a Ti-made autoclave (inner capacity, 1,000 ml). The autoclave was purged with hydrogen under agitation and the internal temperature was elevated to 150° C. Thereafter, 140 ml of benzene was introduced into the autoclave and hydrogenation was conducted with high-speed agitation at a total hydrogen pressure of 50 Kg/cm$^2$G. The results are summaried in Table 7.

TABLE 7

| Run No. | Basic zinc salts | Reaction time (min.) | Conversion of benzene (%) | Selectivity for cyclohexene (%) | Yield of cyclohexene (%) |
| --- | --- | --- | --- | --- | --- |
| 32 | $ZnSO_4.3Zn(OH)_2$ | 90 | 62.2 | 60.6 | 37.7 |
| 33 | $ZnSO_4.4Zn(OH)_2$ | 90 | 58.9 | 63.8 | 37.6 |
| 34 | $ZnSO_4.Zn(OH)_2$ | 90 | 67.0 | 56.7 | 38.0 |
| 35 | $ZnO.3ZnCl_2.H_2O$ | 80 | 65.9 | 46.2 | 30.4 |
| 36 | $3ZnO.ZnCl_2.H_2O$ | 120 | 63.8 | 51.1 | 32.6 |
| 37 | $8ZnO.N_2O_5.4H_2O$ | 140 | 64.3 | 44.8 | 28.8 |

After completion of the reaction carried out in Example 34, the slurry was recovered by filtration and concentrated hydrochloric acid was added to dissolve any zinc compound that would be present on the catalyst and $ZrO_2$. Analysis by plasma emission spectroscopy showed that the solution contained 95 mg of zinc and 18 mg of sulfur. This indicates that a solid basic zinc sulfate had been present in the reaction system used.

EXAMPLES 38-40

Hydrogenation of benzene was conducted as in Examples 32 to 37 except that 30 mg (as Zn) of one of the basic zinc sulfate derivatives shown in Table 8 was used as a basic zinc salt and that water was replaced by 280 ml of a 18 wt. % aqueous solution of $ZnSO_4.7H_2O$. The results are shown below.

| Run No. | Basic zinc sulfate | Reaction time (min.) | Conversion of benzene (%) | Selectivity for cyclohexene (%) | Yield of cyclohexene (%) |
|---|---|---|---|---|---|
| 38 | ZnSO$_4$.3Zn(OH)$_2$ | 30 | 42.8 | 84.4 | 36.1 |
|  |  | 60 | 68.1 | 78.8 | 53.7 |
| 39 | ZnSO$_4$.4Zn(OH)$_2$ | 30 | 40.5 | 85.0 | 34.4 |
|  |  | 60 | 66.5 | 79.0 | 52.5 |
| 40 | ZnSO$_4$.Zn(OH)$_2$ | 30 | 45.6 | 83.1 | 37.9 |
|  |  | 60 | 71.0 | 76.2 | 54.1 |

EXAMPLE 41

Hydrogenation of benzene was conducted as in Examples 32 to 37 except that 30 mg (as Zn) of 3ZnO.ZnCl$_2$.H$_2$O was used as a basic zinc salt and that water was replaced by 280 ml of a 7 wt. % aqueous solution of ZnCl$_2$. The results are shown below.

| Reaction time (min.) | Conversion of benzene (%) | Selectivity for cyclohexene (%) | Yield of cyclohexene (%) |
|---|---|---|---|
| 30 | 38.8 | 76.1 | 29.5 |
| 60 | 64.9 | 70.1 | 45.5 |

EXAMPLE 42

Hydrogenation of benzene was conducted as in Example 38 except that ZrO$_2$ powder was replaced by a HfO$_2$ powder having an average particle size of 1.05 µm. The results are shown below.

| Reaction time (min.) | Conversion of benzene (%) | Selectivity for cyclohexene (%) | Yield of cyclohexene (%) |
|---|---|---|---|
| 30 | 43.3 | 83.0 | 36.1 |
| 60 | 69.0 | 76.7 | 52.9 |

COMPARATIVE EXAMPLE 18

The procedures of Example 38 were repeated except that neither the ZrO$_2$ powder nor ZnSO$_4$.3Zn(OH)$_2$ was employed. The results are shown below.

| Reaction time (min.) | Conversion of benzene (%) | Selectivity for cyclohexene (%) | Yield of cyclohexene (%) |
|---|---|---|---|
| 15 | 40.9 | 70.1 | 28.7 |
| 30 | 67.0 | 52.9 | 35.4 |

After completion of the reaction, the reactor was opened and its interior was observed; the catalyst particles had been agglomerated and deposited on the titanium wall.

COMPARATIVE EXAMPLE 19

The procedures of Example 38 were repeated except that no ZrO$_2$ powder was used. The results are shown below.

| Reaction time (min.) | Conversion of benzene (%) | Selectivity for cyclohexene (%) | Yield of cyclohexene (%) |
|---|---|---|---|
| 40 | 42.7 | 77.7 | 33.2 |
| 80 | 68.0 | 69.5 | 47.3 |

After completion of the reaction, the reactor was opened and its interior was observed; the agglomeration of the catalyst particles was negligible but they had been deposited on the titanium wall.

EXAMPLE 43

The procedures of Example 38 were repeated except that 0.5 g of the catalyst prepared in Example 4 was employed as a hydrogenation catalyst. The results are shown below.

| Reaction time (min.) | Conversion of benzene (%) | Selectivity for cyclohexene (%) | Yield of cyclohexene (%) |
|---|---|---|---|
| 30 | 43.6 | 85.1 | 37.1 |
| 60 | 69.7 | 80.0 | 55.8 |

EXAMPLE 44

The procedures of Example 38 were repeated except that the temperature for hydrogenation was lowered to 120° C. The results are shown below.

| Reaction time (min.) | Conversion of benzene (%) | Selectivity for cyclohexene (%) | Yield of cyclohexene (%) |
|---|---|---|---|
| 60 | 40.0 | 83.3 | 33.3 |
| 120 | 65.7 | 76.1 | 50.0 |

EXAMPLE 45

The procedures of Example 44 were repeated except that ZnSO$_4$.3Zn(OH)$_2$ was not used. The results are shown below.

| Reaction time (min.) | Conversion of benzene (%) | Selectivity for cyclohexene (%) | Yield of cyclohexene (%) |
|---|---|---|---|
| 40 | 38.3 | 73.3 | 28.1 |
| 80 | 64.1 | 58.4 | 37.4 |

EXAMPLE 46

One and a half gram of the same catalyst as used in Example 1 (average crystallite size, 50 Å), 7.5 g of a ZrO$_2$ powder (average particle size, 0.35 µm), 0.6 g (as Zn) of ZnSO$_4$.3Zn(OH)$_2$, and 150 ml of a 18% aqueous solution of ZnSO$_4$.7H$_2$O were charged into an autoclave (inner capacity, 400 ml) the inner surface of which had been coated with Teflon. Hydrogen was introduced into the autoclave to attain a total internal pressure of 50 Kg/cm$^2$G and the charge was agitated at high speed for 200 hours at 160° C. The slurry was recovered and washed. Analysis by X-ray diffraction showed that the catalyst particles of metallic ruthenium had an average crystallite size of 53 Å, which was little different from the initial 50 Å.

One-third of the recovered catalyst was used in preparing a liquid reaction mixture having the same composition as that employed in Example 38, and hydrogenation of benzene was subsequently carried out. The rate of reaction and selectivity for cyclohexene were substantially the same as those attained when the fresh catalyst had been used.

COMPARATIVE EXAMPLE 20

The procedures of Example 46 were repeated except that neither the ZrO$_2$ powder nor ZnSO$_4$.3Zn(OH)$_2$ was used. The recovered catalyst particles of metallic ruthenium had an average crystallite size of 78 Å which was much greater than the initial 50 Å. The time-dependent change of the catalyst was therefore apparent.

One-third of this recovered catalyst was used in preparing a liquid reaction mixture having the same composition (e.g., metal oxide additive) as that employed in Example 38. When hydrogenation of benzene was conducted, the rate of reaction dropped to about one half of the value attained by using the fresh catalyst.

COMPARATIVE EXAMPLE 21

The procedures of Example 46 were repeated except that no ZrO$_2$ powder was used. The recovered metallic ruthenium catalyst had an average crystallite size of 61 Å. One-third of this recovered catalyst was used in preparing a liquid reaction mixture having the same composition (e.g. metal oxide additive) as that employed in Example 38. When hydrogenation of benzene was conducted, the rate of reaction dropped to about three-fourths of the value attained by using the fresh catalyst.

The data obtained in Example 46 and Comparative Examples 20 and 21 clearly show that the hydrogenation catalyst system used in the process of the present invention is extremely stable.

EXAMPLES 47–53

The procedures of Example 38 were repeated except that the amount of the 18 wt. % aqueous solution of ZnSOhd 4.7H$_2$O used, the amount of benzene used, and the reaction temperature and pressure were changed as shown in Table 8. The results are also shown in Table 8.

EXAMPLES 54–56

The procedures of Example 38 were repeated except that benzene used as a monocyclic aromatic hydrocarbon feed was replaced by toluene, p-xylene or ethylbenzene. The results are shown in Table 9.

TABLE 9

| Run No. | Feed | Reaction time (min.) | Conversion of feed (%) | Selectivity for cycloolefin* (%) | Yield of cycloolefin* (%) |
|---|---|---|---|---|---|
| 54 | toluene | 100 | 58.2 | 74.3 | 43.2 |
| 55 | p-xylene | 180 | 57.7 | 71.4 | 41.2 |
| 56 | ethylbenzene | 150 | 55.5 | 75.2 | 41.7 |

*The total of cycloolefin isomers produced.

TABLE 8

| Run No. | Amount of benzene (ml) | Amount of aqueous solution ZnSO$_4$.7H$_2$O (ml) | Reaction temperature (°C.) | Reaction pressure (Kg/cm$^2$G) | Reaction time (min.) | Conversion of benzene (%) | Selectivity for cyclohexene (%) | Yield of cyclohexene (%) |
|---|---|---|---|---|---|---|---|---|
| 47 | 200 | 200 | 150 | 50 | 80 | 66.3 | 76.8 | 50.9 |
| 48 | 280 | 140 | 150 | 50 | 100 | 67.7 | 70.2 | 47.5 |
| 49 | 320 | 80 | 150 | 50 | 110 | 65.0 | 60.2 | 39.1 |
| 50 | 400 | 0 | 150 | 50 | 10 | 52.7 | 7.1 | 3.7 |
| 51 | 140 | 280 | 180 | 50 | 50 | 74.3 | 66.1 | 49.1 |
| 52 | 140 | 280 | 150 | 90 | 60 | 70.2 | 79.2 | 55.6 |
| 53 | 140 | 280 | 150 | 20 | 90 | 54.3 | 60.1 | 32.6 |

What is claimed is:

1. A process for producing a cycloolefin which comprises partially hydrogenating a monocyclic aromatic hydrocarbon with hydrogen under neutral or acidic conditions in the presence of:
   (i) water,
   (ii) a particulate hydrogenating catalyst comprising at least 60% by weight metallic ruthenium having an average crystallite size of 200 Å or less, said catalyst being dispersed in an aqueous phase,
   (iii) at least one zinc salt as a promotor, and
   (iv) at least one additive particle selected from the group consisting of oxides, hydroxides and hydrates of Zr, Hf, Ti, Nb, Ta, Cr, Fe, Co, Al, Ga, and Si; and wherein said additive particle is not a support for said catalyst.

2. A process according to claim 1, wherein the metallic ruthenium has an average crystallite size of 100 Å or less.

3. A process according to claim 1, wherein the particulate hydrogenating catalyst is prepared by reducing a zinc-containing ruthenium compound.

4. A process according to claim 3, wherein the particulate hydrogenating catalyst contains 0.1–50% by weight of zinc based on the metallic ruthenium.

5. A process according to claim 4, wherein the particulate hydrogenating catalyst contains 2–20% by weight of zinc based on the metallic ruthenium.

6. A process according to claim 1, wherein the particulate hydrogenating catalyst is prepared by reducing an iron-containing ruthenium compound.

7. A process according to claim 6, wherein the particulate hydrogenating catalyst contains 0.01–50% by weight of iron based on the metallic ruthenium.

8. A process according to claim 7, wherein the particulcate hydrogenating catalyst contains 0.1–20% by weight of iron based on the metallic ruthenium.

9. A process according to claim 1, wherein the particulate hydrogenating catalyst is used in an amount of 0.001–50% by weight based on the monocyclic aromatic hydrocarbon.

10. A process according to claim 9, wherein the particulate hydrogenating catalyst is used in an amount of 0.01–20% by weight based on the monocyclic aromatic hydrocarbon.

11. A process according to claim 1, wherein the promoter is a water-soluble zinc salt.

12. A process according to claim 11, wherein the concentration of the water-soluble zinc salt in the water ranges from $1 \times 10^{-3}$% by weight to the saturated concentration thereof.

13. A process acoording to claim 11, wherein said zinc salt is a zinc salt of a strong acid.

14. A process according to claim 11, wherein said zinc salt is zinc sulfate.

15. A process according to claim 14, wherein the concentration of zinc sulfate in the water ranges from 0.1 to 30% by weight.

16. A process according to claim 1, wherein the promoter is a solid basic zinc salt.

17. A process according to claim 16, wherein the solid basic zinc compound is present in an amount as zinc element which ranges from $1 \times 10^{-4}$ to 1 times by weight based on the weight of the total amount of the particulate hydrogenating catalyst and the additive.

18. A process according to claim 16, wherein the solid basic zinc salt is a solid basic zinc sulfate.

19. A process according to claim 18, wherein the solid basic zinc sulfate is present in an amount as zinc element which ranges from $1 \times 10^{-3}$ to 0.5 times by weight based on the weight of the total amount of the particulate hydrogenating catalyst and the additive.

20. A process according to claim 1, wherein the promoter consists of at least one zinc salt of a strong acid and at least one solid basic zinc salt.

21. A process according to claim 20, wherein the concentration of the zinc salt of a strong acid in the water ranges from $1 \times 10^{-3}$% by weight to the saturated concentration thereof and the solid basic zinc salt is present in an amount as zinc element which ranges from $1 \times 10^4$ to 1 times by weight based on the weight of the total amount of the particulate hydrogenating catalyst and the additive.

22. A process according to claim 20, wherein the zinc salt of a strong acid is zinc sulfate and the solid basic zinc salt is a solid basic zinc sulfate.

23. A process according to claim 1 wherein the additive has an average particle size of 0.005–100 μm.

24. A process according to claim 24, wherein the additive has an average particle size of 0.005–10 82 m.

25. A process according to claim 1, wherein the amount of the additive ranges from $1 \times 10^{-3}$ to 0.3 times by weight based on the weight of the water.

26. A process according to claim 25, wherein the amount of the additive ranges from $1 \times 10^{-2}$ to 0.1 times by weight based on the weight of the water.

27. A process according to claim 1, wherein the additive is zirconium oxide or hafnium oxide.

28. A process according to claim 1, wherein the amount of water ranges from 0.01 to 100 times by weight based on the weight of the monocyclic aromatic hydrocarbon.

29. A process according to claim 28, wherein the amount of water ranges from 0.5 to 20 times by weight based on the weight of the monocyclic aromatic hydrocarbon.

30. A process according to claim 1, wherein the partial hydrogenation of the monocyclic aromatic hydrocarbon is carried out at a pH value from 0.5 to less than 7.

31. A process according to claim 31, wherein the pH value ranges from 2 to 6.5.

32. A process according to claim 1, wherein the monocyclic aromatic hydrocarbon is selected from among benzene, toluene, o-xylene, m-xylene, p-xylene and ethylbenzene.

33. A process according to claim 32, wherein the monocyclic aromatic hydrocarbon is benzene.

34. A process according to claim 1, wherein the partial hydrogenation of the monocyclic aromatic hydrocarbon is carried out at a temperature of 20° to 250° C.

35. A process according to claim 34, wherein the temperature ranges from 100° to 200° C.

36. A process according to claim 1, wherein the partial hydrogenation of the monocyclic aromatic hydrocarbon is carried out at a hydrogen pressure of 1 to 200 Kg/cm²G.

37. A process according to claim 36, wherein the hydrogen pressure ranges from 10 to 100 Kg/cm² G.

* * * * *